(12) United States Patent
Araújo Martins Vilaça et al.

(10) Patent No.: US 12,397,171 B2
(45) Date of Patent: Aug. 26, 2025

(54) DEVICE FOR LASER SKIN TREATMENT

(71) Applicant: IPCA—Instituto Politécnico do Cávado e do Ave, V Frescainha (PT)

(72) Inventors: João Luís Araújo Martins Vilaça, V Frescainha (PT); Bruno Miguel Gomes Oliveira, V Frescainha (PT); Pedro André Gonçalves Morais, V Frescainha (PT); Fernando José Da Silva Veloso, V Frescainha (PT); António Herculano Jesus Moreira, V Frescainha (PT); António Lúcio De Azevedo Miranda Baptista, V Frescainha (PT); Jaime Francisco Cruz Fonseca, V Frescainha (PT)

(73) Assignee: IPCA—INSTITUTO POLITÉCNICO DO CÁVADO E DO AVE, V Frescainha (PT)

( * ) Notice: Subject to any disclaimer, the term of this patent is extended or adjusted under 35 U.S.C. 154(b) by 527 days.

(21) Appl. No.: 17/764,372

(22) PCT Filed: Sep. 29, 2020

(86) PCT No.: PCT/IB2020/059109
§ 371 (c)(1),
(2) Date: Mar. 28, 2022

(87) PCT Pub. No.: WO2021/059255
PCT Pub. Date: Apr. 1, 2021

(65) Prior Publication Data
US 2022/0339465 A1 Oct. 27, 2022

(30) Foreign Application Priority Data
Sep. 29, 2019 (PT) .......................... 115802

(51) Int. Cl.
*A61N 5/06* (2006.01)
*A61N 5/067* (2006.01)

(52) U.S. Cl.
CPC ........... *A61N 5/0616* (2013.01); *A61N 5/067* (2021.08); *A61N 2005/0626* (2013.01); *A61N 2005/0632* (2013.01); *A61N 2005/0664* (2013.01)

(58) Field of Classification Search
CPC .................. A61N 5/0616; A61N 5/067; A61N 2005/0626
See application file for complete search history.

(56) References Cited

U.S. PATENT DOCUMENTS 9,833,254 B1 12/2017 Barral et al.

FOREIGN PATENT DOCUMENTS

DE 102017116004 A1 1/2019
FR 3076994 A1 7/2019

OTHER PUBLICATIONS

International Search Report for corresponding PCT Application No. PCT/IB2020/059109 mailed on Feb. 1, 2021.

(Continued)

*Primary Examiner* — Paula J Stice
(74) *Attorney, Agent, or Firm* — Leason Ellis LLP

(57) ABSTRACT

Device and operation method thereof for laser skin treatment of skin features extending along a path, in particular veins, by collaborative motion between an operator and a robotic support, comprising: a skin, in particular vascular, further in particular vein, treatment laser head having a laser beam target line, and a robotic support of said laser head; further comprising, attached to the laser head or to the robotic support where the laser head is supported: a camera for capturing skin surface images, one or more handles for handling by the operator, a force sensor for sensing the (Continued)

intensity and direction of force applied to the handle or handles by the operator for controlling the robotic support, and an electronic data processor configured for carrying out the steps comprising: capturing an image of skin surface comprising a skin feature to be treated; identifying, from said captured image and proximal to where the laser beam target line intersects the skin surface, the path of the skin feature to be treated; applying, through the robotic support, a transversal force, to the laser head along a transversal direction to said path and towards said path; while allowing freely controllable movement of the robotic support by the operator along the direction of said path.

19 Claims, 11 Drawing Sheets

(56) References Cited

OTHER PUBLICATIONS

M. Adamič et al., "Guidelines of care for vascular lasers and intense pulse light sources from the European Society for Laser Dermatology," J. Eur. Acad. Dermatol. Venereol., Sep. 2015, pp. 1661-1678, vol. 29.

J. L. Vilaça et al., "Calibration procedure for 3D measurement systems using two cameras and a laser line," Opt. Laser Technol., Mar. 2009, pp. 112-119, vol. 41.

Z. Zhang, "A flexible new technique for camera calibration," IEEE Trans. Pattern Anal. Mach. Intell., Nov. 2000, pp. 1330-1334, vol. 22.

Jian Liang et al., "Camera-Based Document Image Mosaicing," Aug. 2006, pp. 476-479.

Brown and Lowe, "Recognising panoramas," Oct. 2003, pp. 1218-1225 vol. 2.

K. Yen and M. H. Gorelick, "New Biomedical Devices That Use Near-Infrared Technology to Assist With Phlebotomy and Vascular Access," Pediatr. Emerg. Care, Mar. 2013, pp. 383-385, vol. 29.

Y. Li et al., "A Novel Method for Low-Contrast and High-Noise Vessel Segmentation and Location in Venipuncture," EEE Trans. Med. Imaging, Nov. 2017, pp. 2216-2227, vol. 36.

R. Fernández and M. Armada, "Multisensory System for the Detection and Localization of Peripheral Subcutaneous Veins," Sensors, Apr. 2017, p. 897, vol. 17.

A. Chen et al., "Portable robot for autonomous venipuncture using 3D near infrared image guidance," Technology, Sep. 2013, pp. 72-87, vol. 01.

D. Ai et al., "Augmented reality based real-time subcutaneous vein imaging system," Biomed. Opt. Express, Jul. 2016, p. 2565, vol. 7.

R. K. Miyake et al., "Vein Imaging: A New Method of Near Infrared Imaging, Where a Processed Image Is Projected onto the Skin for the Enhancement of Vein Treatment," Dermatol. Surg., Aug. 2006, pp. 1031-1038, vol. 32.

V. P. Zharov et al., "Infrared imaging of subcutaneous veins," Lasers Surg. Med., Jan. 2004, pp. 56-61, vol. 34.

R. A. Beasley, "Medical Robots: Current Systems and Research Directions," J. Robot., Oct. 2012, pp. 1-14.

J. Burgner-Kahrs et al., "Continuum Robots for Medical Applications: A Survey," IEEE Trans. Robot., Dec. 2015, pp. 1261-1280, vol. 31.

DEVICE FOR LASER SKIN TREATMENT

CROSS-REFERENCE TO RELATED APPLICATIONS

This application is a U.S. National Stage Application under 35 U.S.C. § 371 of International Patent Application No. PCT/IB2020/059109, filed Sep. 29, 2020, which claims priority to Portugal Patent Application No. 115802, filed Sep. 29, 2019, the contents of which are each hereby incorporated by reference in their respective entireties.

TECHNICAL FIELD

The present disclosure relates to a laser device and a method for operating said device for light-based skin treatment.

BACKGROUND

Chronic venous disorders (CVD) of lower limbs affect millions of people worldwide. Specifically, for telangiectasias and reticular veins, which represent more than 50% of all CVD, laser-based therapies are usually used. Despite their considerable advantages, treatment safety and efficacy depend on the correct identification of unhealthy veins and on the correct handling of the laser device. However, laser guidance is usually performed through a naked eye evaluation, making the correct application of this therapy challenging and dependent on the user expertise.

Chronic venous disorders (CVD) of lower limbs is a condition associated or caused by veins that become abnormal/unhealthy in this body region, resulting from incompetent valves, venous obstruction or muscle pump dysfunction. Recent studies showed a prevalence of CVD around 80% in adults, making it one of the most common chronic medical conditions reported worldwide. Among all CVD, telangiectasias and reticular veins are the most common in adults with a prevalence higher than 50%. These disorders affect the appearance and self-esteem of millions of persons, and their treatment is a common dermatologic request.

Over the years, there has been a huge interest in developing an effective, safety and non-invasive strategy to treat telangiectasias and reticular veins. In this scope, laser therapy has been implemented and is now widely used for the treatment of several vascular lesions. This therapy is based upon the laser's ability to supply a destructive dose of thermal energy to affected tissues. Specifically, for the treatment of leg veins, top results can now be achieved using laser. In these, the ability to selectively target specific structures is made possible by adjusting several laser parameters, including its wavelength, spot size, cooling, pulse time, and power.

Several clinical studies have been made to understand how these parameters should be adjusted to achieve the best performance for laser-based treatment of leg veins. These adjustments depend on the correct identification and segmentation of the vascular lesion (e.g. size, colour), as well as on the correct handling of the laser (e.g. distance/angle, vessel-centred). However, in clinical practice, naked-eye evaluation is still widely used to select the optimal parameters and to handle the device, being the treatment outcome highly dependent on the physician's expertise. Indeed, an incorrect use of the laser device reduces the treatment effectiveness and is the cause of several side effects, including discolouration, hypopigmentation, skin texture changes, and scarring.

Overall, a system that guarantees or markedly improves the correct handling of the laser during the entire treatment, minimizes the side effects of this treatment, improve its effectiveness and reduces the operator learning curvature, having the potential to be widely well accepted in a large number of laser/light-base treatments, representing a market share of more than 12 billion dollars in sales worldwide.

These facts are disclosed in order to illustrate the technical problem addressed by the present disclosure.

References

[1] M. Adamič, M. D. Pavlović, A. Troilius Rubin, M. Palmetun-Ekbäck, and P. Boixeda, "Guidelines of care for vascular lasers and intense pulse light sources from the European Society for Laser Dermatology," J. Eur. Acad. Dermatol. Venereol., vol. 29, no. 9, pp. 1661-1678, September 2015.

[2] J. L. Vila a, J. C. Fonseca, and A. M. Pinho, "Calibration procedure for 3D measurement systems using two cameras and a laser line," Opt. Laser Technol., vol. 41, no. 2, pp. 112-119, March 2009.

[3] Z. Zhang, "A flexible new technique for camera calibration," IEEE Trans. Pattern Anal. Mach. Intell., vol. 22, no. 11, pp. 1330-1334, November 2000.

[4] Jian Liang, D. DeMenthon, and D. Doermann, "Camera-Based Document Image Mosaicing," 2006, pp. 476-479.

[5] Brown and Lowe, "Recognising panoramas," 2003, pp. 1218-1225 vol. 2.

[6] K. Yen and M. H. Gorelick, "New Biomedical Devices That Use Near-Infrared Technology to Assist With Phlebotomy and Vascular Access," Pediatr. Emerg. Care, vol. 29, no. 3, pp. 383-385, 2013.

[7] Y. Li et al., "A Novel Method for Low-Contrast and High-Noise Vessel Segmentation and Location in Venipuncture," IEEE Trans. Med. Imaging, vol. 36, no. 11, pp. 2216-2227, November 2017.

[8] R. Fernandez and M. Armada, "Multisensory System for the Detection and Localization of Peripheral Subcutaneous Veins," Sensors, vol. 17, no. 12, p. 897, April 2017.

[9] A. Chen, K. Nikitczuk, J. Nikitczuk, T. Maguire, and M. Yarmush, "Portable robot for autonomous venipuncture using 3D near infrared image guidance," TECHNOLOGY, vol. 01, no. 01, pp. 72-87, September 2013.

[10] D. Ai et al., "Augmented reality based real-time subcutaneous vein imaging system," Biomed. Opt. Express, vol. 7, no. 7, p. 2565, July 2016.

[11] R. K. Miyake et al., "Vein Imaging: A New Method of Near Infrared Imaging, Where a Processed Image Is Projected onto the Skin for the Enhancement of Vein Treatment," Dermatol. Surg., vol. 32, no. 8, pp. 1031-1038, August 2006.

[12] V. P. Zharov, S. Ferguson, J. F. Eidt, P. C. Howard, L. M. Fink, and M. Waner, "Infrared imaging of subcutaneous veins," Lasers Surg. Med., vol. 34, no. 1, pp. 56-61, January 2004.

[13] R. A. Beasley, "Medical Robots: Current Systems and Research Directions," J. Robot., vol. 2012, pp. 1-14, 2012.

[14] J. Burgner-Kahrs, D. C. Rucker, and H. Choset, "Continuum Robots for Medical Applications: A Survey," IEEE Trans. Robot., vol. 31, no. 6, pp. 1261-1280, December 2015.

GENERAL DESCRIPTION

This disclosure includes a method and device for guidance of light-based treatments for leg veins. Such tool provides an automatic identification of unhealthy veins and a collaborative robotic handling during the treatment session. Thus, with the introduction of this technology, a minimization of side-effects and improvement of treatment effectiveness is obtained. Moreover, a reduction on the learning curvature is also obtained, broadening the procedure to novice users.

This disclosure includes a device and method that combine real-time segmentation of vascular lesions with a collaborative robot for laser treatment. The proposed strategy helps the physician to maintain an optimal laser handling throughout the entire treatment session. Thus, the main goals/contributions of this disclosure include:

- Development of a strategy for vascular lesions identification and segmentation from image acquisition systems (e.g. RGB, near-infrared camera—NIR); Design and development of a user-friendly augmented reality interface for real-time guidance of the laser treatment;
- Development of a method to recognize the limits of the lesion to treatment, consequently minimizing side effects related with over-treatment;
- Development of local control strategies for collaborative robotic laser guidance based on the location of the lesion to treat (laser/skin distance and angle, laser/pathologic vein positioning), to improve the handling precision and accuracy of the laser;
- Development of a handheld gripper device to interact with the collaborative robot, which may include RGB/NIR/3D sensors and the laser device;
- Creation of a setup that simulates a real scenario of laser treatment for leg veins, allowing the validation of the disclosure.

It is disclosed a device for laser skin treatment of skin features extending along a path, in particular veins, by collaborative motion between an operator and a robotic support, comprising: a skin, in particular vascular, further in particular vein, treatment laser head having a laser beam target line, and a robotic support of said laser head; further comprising, attached to the laser head or to the robotic support where the laser head is supported:
- a camera for capturing skin surface images,
- one or more handles for handling by the operator,
- a force sensor for sensing the intensity and direction of force applied to the handle or handles by the operator for controlling the robotic support, and
- an electronic data processor configured for carrying out the steps comprising:
- capturing an image of skin surface comprising a skin feature to be treated;
- identifying, from said captured image and proximal to where the laser beam target line intersects the skin surface, the path of the skin feature to be treated;
- applying, through the robotic support, a transversal force, to the laser head along a transversal direction to said path and towards said path;
- while allowing freely controllable movement of the robotic support by the operator along the direction of said path.

In an embodiment, said laser head comprises one or more lasers and/or one or more wavelengths.

In an embodiment, said vascular lesions can be a lesion or other laser procedures where a physical and/or virtual path is followed, namely hair removal, tattoo removal, scar removal, among similar. The virtual path is preferably predefined to extend along the target region such that the treated area by laser spot along the virtual path covers the target region.

In an embodiment, said transversal direction is parallel to the skin surface.

In an embodiment, the electronic data processor is further configured for maintaining, through the robotic support, a first transversal distance between said path and where the laser beam target line intersects the skin surface,
  wherein said first transversal distance varies positively with a first force as measured by said force sensor along said transversal direction parallel to the skin surface.

In an embodiment, said first transversal distance is directly proportional to said force.

In an embodiment, the electronic data processor is further configured for applying, through the robotic support, said transversal force, to the laser head along a transversal direction to said path and towards said path, to maintain, constant and equal to a predetermined amount, the first transversal distance between said path and where the laser beam target line intersects the skin surface.

In an embodiment, the electronic data processor is further configured for maintaining, through the robotic support, a second transversal distance between said laser head and skin surface, along a further transversal direction, wherein said further transversal direction is perpendicular to the skin surface, and
  wherein said second transversal distance, offset by a predetermined amount of distance, varies positively with a second force as measured by said force sensor along said further transversal direction perpendicular to the skin surface.

In an embodiment, said second transversal distance is directly proportional to said further force.

In an embodiment, the proportionality constant of the first transversal distance relative to the first force and the proportionality constant of the second transversal distance relative to the second force are different,
  in particular the proportionality constant of the first transversal distance relative to the first force is higher than the proportionality constant of the second transversal distance relative to the second force.

In an embodiment, the electronic data processor is further configured for applying, through the robotic support, a further force to said laser head along a further transversal direction to said path and towards said path, wherein said further transversal direction is perpendicular to the skin surface, such that a second transversal distance between laser head and skin surface is kept constant and equal to a predetermined amount.

In an embodiment, the electronic data processor is further configured for applying, through the robotic support, a further force to said laser head along a further transversal direction to said path and where the laser beam target line intersects the skin surface, such that a second transversal distance between laser head and the laser beam target line is kept constant and equal to a predetermined amount.

In an embodiment, the electronic data processor is further configured for maintaining, through the robotic support, a first angular displacement of the laser beam head about the longitudinal direction to said path, wherein said angular displacement varies positively with a first torque as measured by said force sensor along said longitudinal direction to the said path.

In an embodiment, the electronic data processor is further configured for maintaining, through the robotic support, a second angular displacement between laser beam head and a transversal direction to said path which is perpendicular to the skin surface, wherein said angular displacement varies positively with a second torque as measured by said force sensor along said transversal direction.

In an embodiment, the electronic data processor is further configured for maintaining, through the robotic support, a third angular displacement between laser beam head and a transversal direction to said path which is parallel to the skin surface, wherein said angular displacement varies positively with a third torque as measured by said force sensor along said transversal direction.

In an embodiment, said electronic data processor is further configured for applying a speed dampening to the movement of the robotic support which is inversely related to the speed of the laser head.

In an embodiment, said transversal force is determined by an impedance control in respect of the transversal distance, parallel to the skin surface, between said path and where the laser beam target line intersects the skin surface, versus the force applied by the operator in said transversal direction parallel to the skin surface.

In an embodiment, said transversal force is determined by an impedance control in respect of the transversal distance, perpendicular to the skin surface, between said laser head and skin surface, offset by a predetermined amount of distance, versus the force applied by the operator in said transversal direction perpendicular to the skin surface.

In an embodiment, said torque is determined by an impedance control in respect of the angular displacement between the laser beam head and the longitudinal direction to the said path, versus the torque applied by the operator in said angular displacement.

In an embodiment, said torque is determined by an impedance control in respect of the angular displacement between the laser beam head and a transversal direction to said path which is perpendicular to the skin surface, versus the torque applied by the operator in said angular displacement.

In an embodiment, said torque is determined by an impedance control in respect of the angular displacement between the laser beam head and a transversal direction to said path which is parallel to the skin surface, versus the torque applied by the operator in said angular displacement.

In an embodiment, the electronic data processor is further configured for applying, through the robotic support, a longitudinal force to said laser head along a longitudinal direction along said path, wherein said force is determined by an impedance control in respect of the longitudinal distance along said path from a predetermined treatment point in respect of the force applied by the operator in said longitudinal direction, wherein the transversal movement stiffness is higher than the longitudinal movement stiffness.

In an embodiment, there are a plurality of predetermined treatment points along said path, and the distance between predetermined treatment points is kept constant and equal to a predetermined amount.

In an embodiment, the electronic data processor is further configured for applying through the robotic support a torque to said laser head, such that the angle between the beam of the laser head and skin surface is kept perpendicular.

In an embodiment, the electronic data processor is further configured for applying, through the robotic support, a force to said laser head longitudinally to said path such that the laser head is freely movable along said path by the operator using said handle or handles.

In an embodiment, the electronic data processor is further configured for applying, through the robotic support, a force to said laser head longitudinally to said path such that the distance between the laser head and the current treatment point is kept constant and equal to a predetermined amount.

In an embodiment, said longitudinal force is determined by an impedance control in respect of the distance between laser beam head and the current treatment point, versus the force applied by the operator in said direction.

In an embodiment, the electronic data processor is further configured for applying, through the robotic support, a force to said laser head along a direction between the point where the laser beam target line intersects the skin surface and the current treatment point wherein the movement stiffness is defined to apply a smooth movement towards the said current treatment point.

In an embodiment, the robotic support is a robotic arm, in particular a robotic arm including 6 or 7 degrees of freedom.

An embodiment comprises a sloped base for holding the robotic support, wherein the sloped base is inclined towards the treatment area.

In an embodiment, the skin features extending along a path include a linear portion of a scar or a linear portion of a tattoo. When applying laser treatment extending along a path, the laser spot size may be sized for covering the width of the linear scar/tattoo portion.

In an embodiment, the electronic data processor is further configured for using low tolerance configurations of the robotic arm degrees of freedom.

An embodiment comprises a Near-InfraRed, NIR, camera for vein image capture enhancement. A NIR camera can capture and/or enhance vein images up to a few millimetres inside the skin. This is advantageous for the present disclosure because there is an improved vein visualization.

An embodiment comprises a VISible light, VIS, camera for skin surface image capture.

The force sensor can sense the intensity and direction of force applied to the handle or handles by the operator, either directly on the handle or handles, or indirectly by sensing the intensity and direction of force applied by the operator to a joystick mounted on the handle or handles.

An embodiment comprises a force sensor that measures the force applied by the user directly in the robotic support of said laser head and/or in a joystick.

In an embodiment, the electronic data processor is further configured for combining the NIR and VIS captured images.

An embodiment comprises a stereoscopic camera, a LIDAR camera or a structured light camera for 3D capture of the skin surface.

An embodiment comprises 3 or more laser rangefinders arranged at, or in the vicinity of, the laser head for determining the distance between the laser head and the skin surface, and/or for determining the angle between the laser head beam and the skin surface.

An embodiment comprises 3 or more laser rangefinders arranged at, or in the vicinity of, the laser head in order to overlay the rangefinder laser spots in the captured skin surface image for determining pixel size of the skin surface image and/or for aligning the captured skin surface image with the laser head.

In an embodiment, the an electronic data processor is further configured for applying through the robotic support a force to said laser head along a transversal direction to said path and towards said path, wherein said transversal direction is perpendicular to the skin surface, such that the distance between laser head and skin surface is kept constant and equal to a predetermined amount minus a predetermined vein depth.

A positive relationship, or varying positively with, defines a relationship between two variables in which as one increases, the other also increases; and reversely as one decreases, the other also decreases.

Impedance control is a generalization of stiffness control. It establishes a dynamical relationship between the position of the laser head and the force, and provide a manipulator control in free-space and in compliant motion with environmental contact. There are different ways of implementing impedance control, namely impedance control and admittance control.

Mechanical impedance referrers to a physical system that accepts motion inputs and yields force outputs.

Mechanical admittance is defined as a physical system that accepts force inputs and yields motion outputs.

Mechanical impedance can have a spring constant component and a damping constant component. A "spring constant" can be defined as a proportionality constant that defines the force output for a tension or compression of the spring. A "damping constant" can also be defined as a force output for a velocity input.

BRIEF DESCRIPTION OF THE DRAWINGS

The following figures provide preferred embodiments for illustrating the disclosure and should not be seen as limiting the scope of invention.

DETAILED DESCRIPTION

Figure 1:
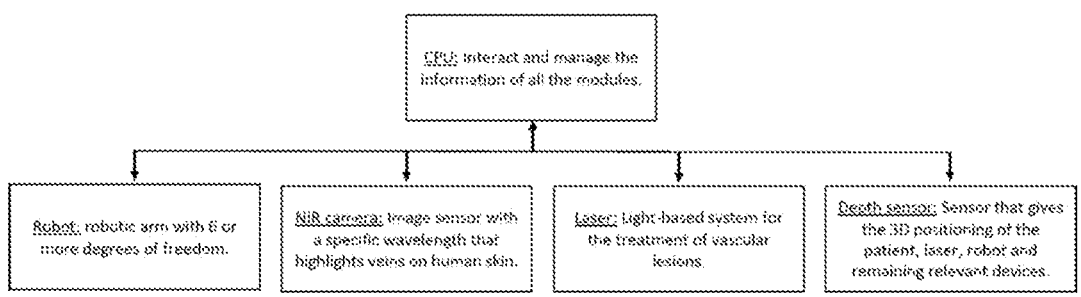
FIG. 1: Schematic representation according to an embodiment of the disclosure of main device modules.
Figure 2:
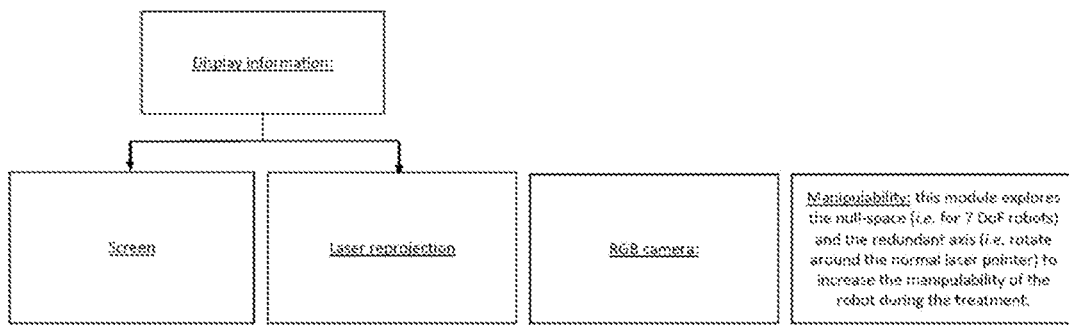
FIG. 2: Schematic representation according to an embodiment of the disclosure of further device modules.
Figure 3:
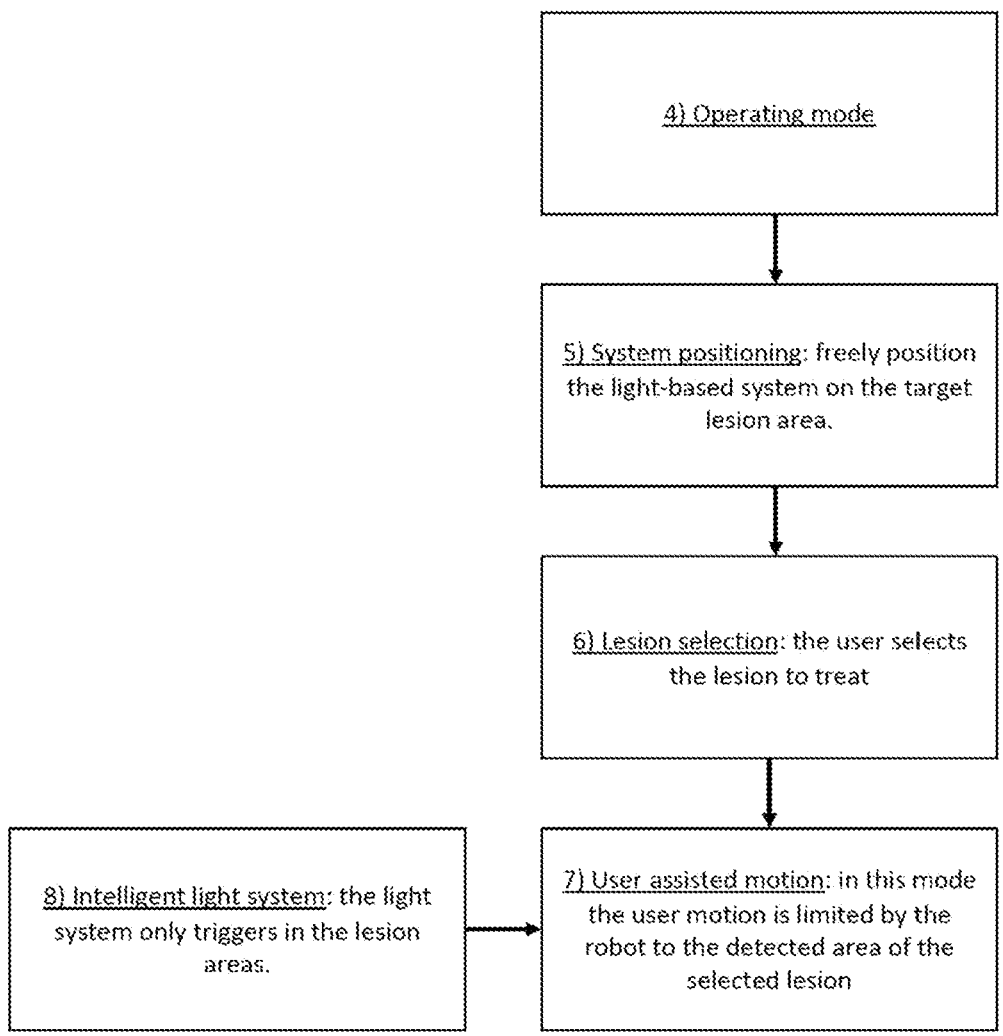
FIG. 3: Schematic representation according to an embodiment of the disclosure of a main device workflow.
Figure 4:
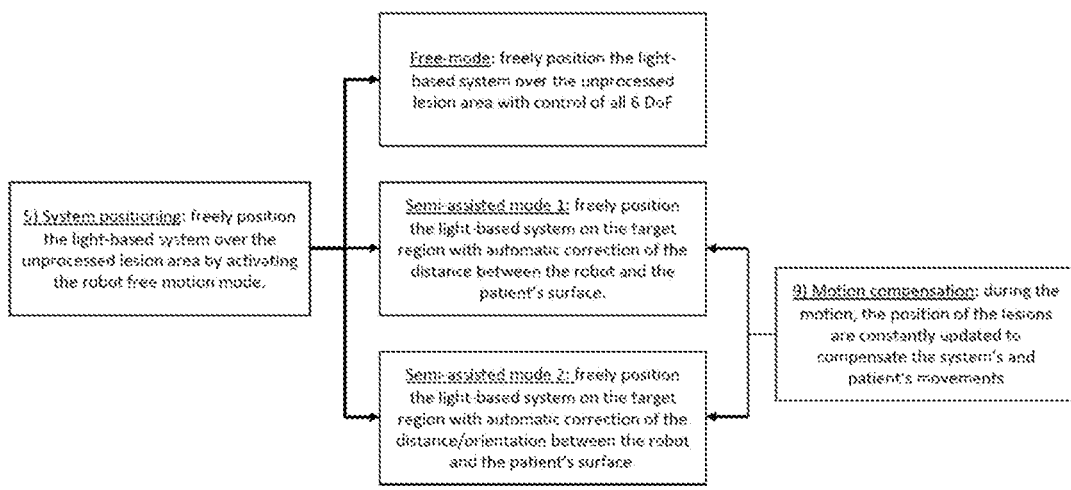
FIG. 4: Schematic representation according to an embodiment of the disclosure of alternatives for positioning operation method.
Figure 5:
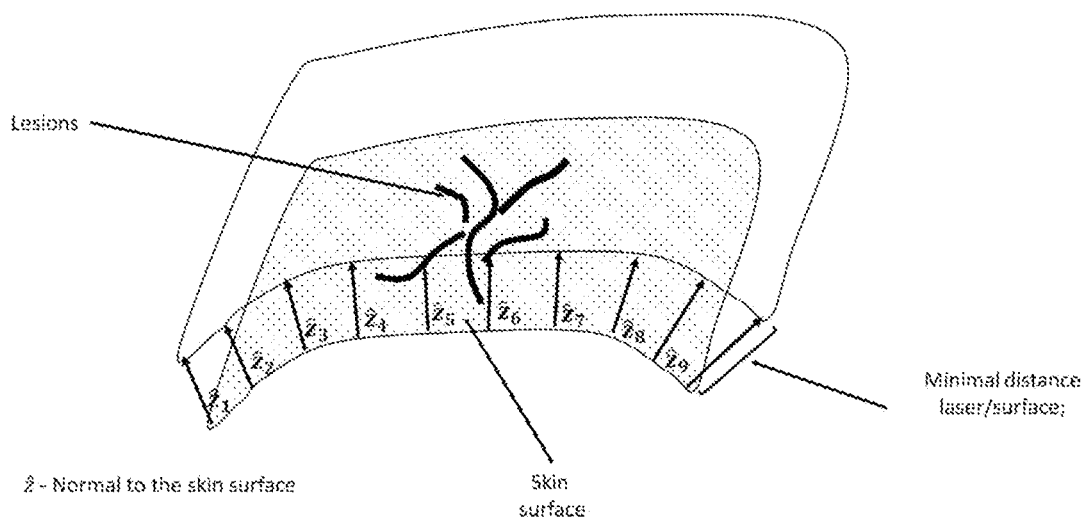
FIG. 5: Schematic illustration according to an embodiment of the disclosure of work zone limitation in terms of distance form skin measured perpendicularly to the skin surface.
Figure 6:
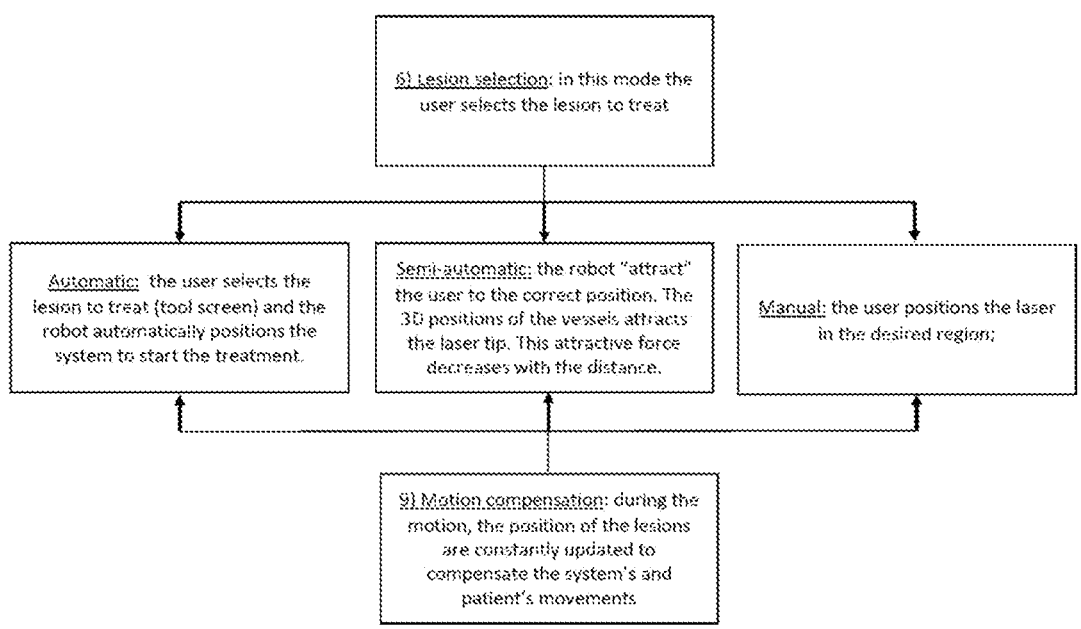
FIG. 6: Schematic representation according to an embodiment of the disclosure of a lesion selection operation method.
Figure 7:
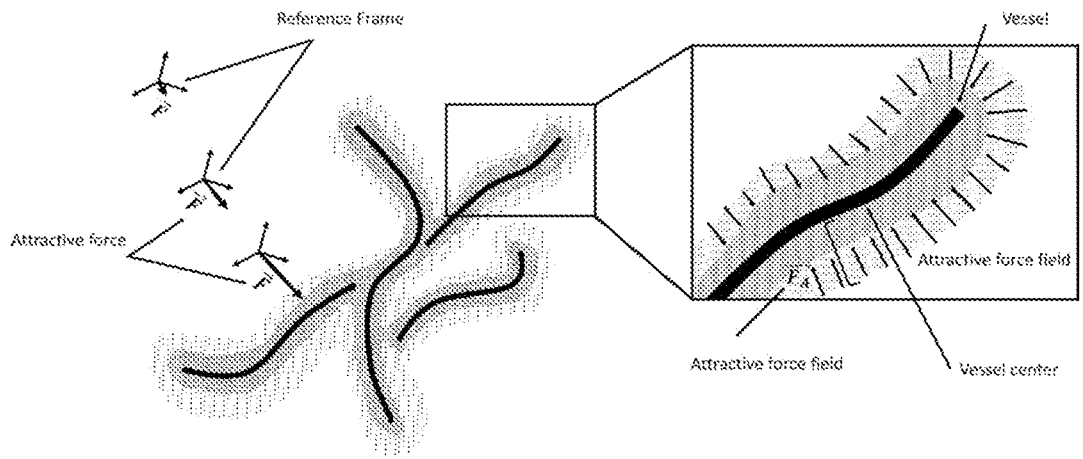
FIG. 7: Schematic illustration according to an embodiment of the disclosure of an operation method for causing an attractive force towards a vein path.
Figure 8:
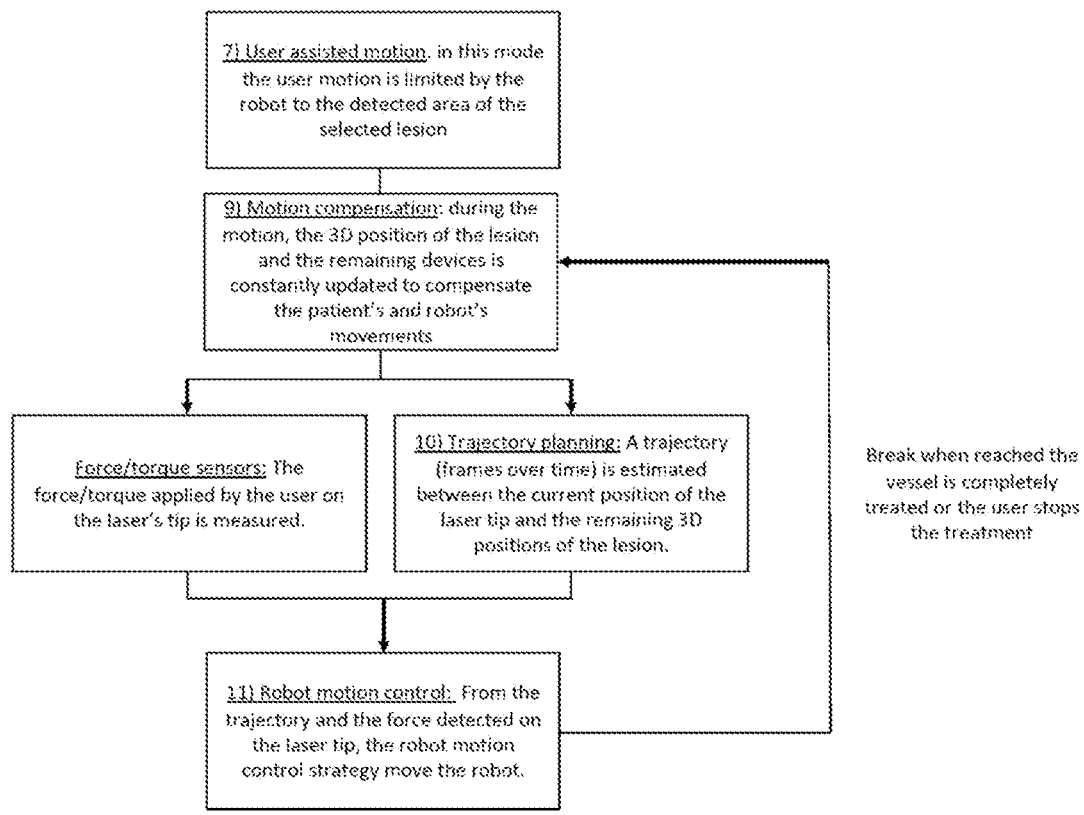
FIG. 8: Schematic representation according to an embodiment of the disclosure of an operation method for user assisted motion.
Figure 9:
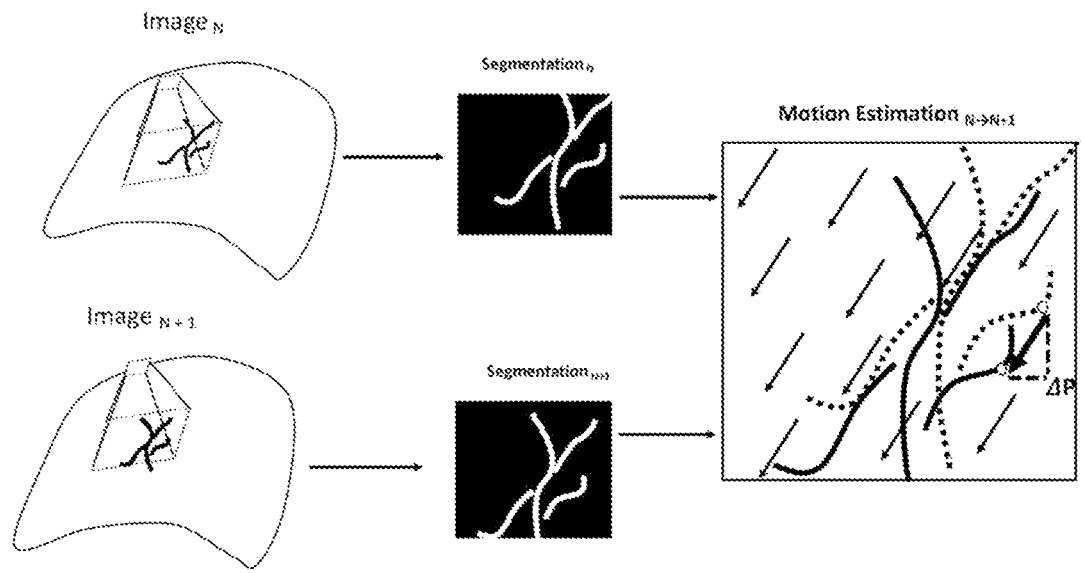
FIG. 9: Schematic illustration according to an embodiment of the disclosure of an image processing and tracking operation method.
Figure 10:
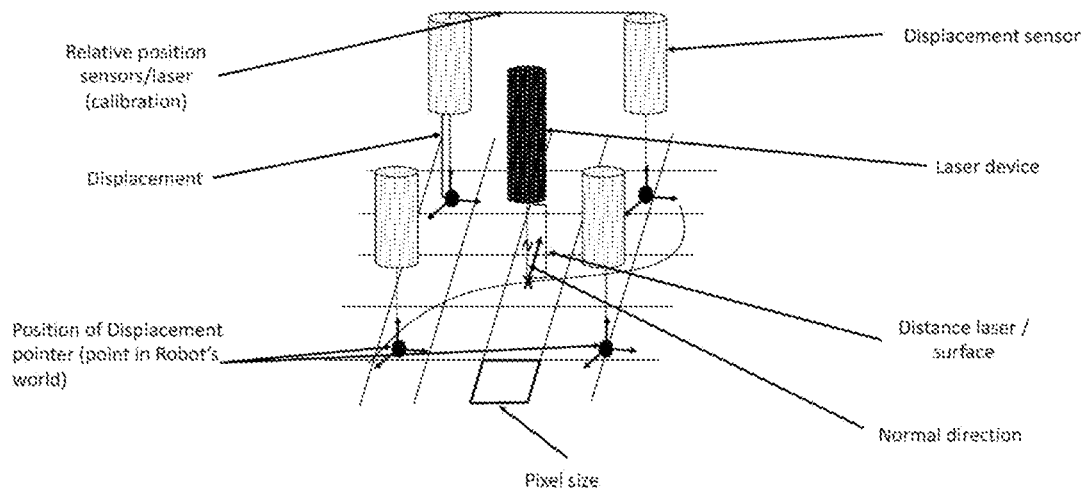
FIG. 10: Schematic illustration according to an embodiment of the disclosure of an operation method for 3D positioning with laser-base displacement sensors.
Figure 11:
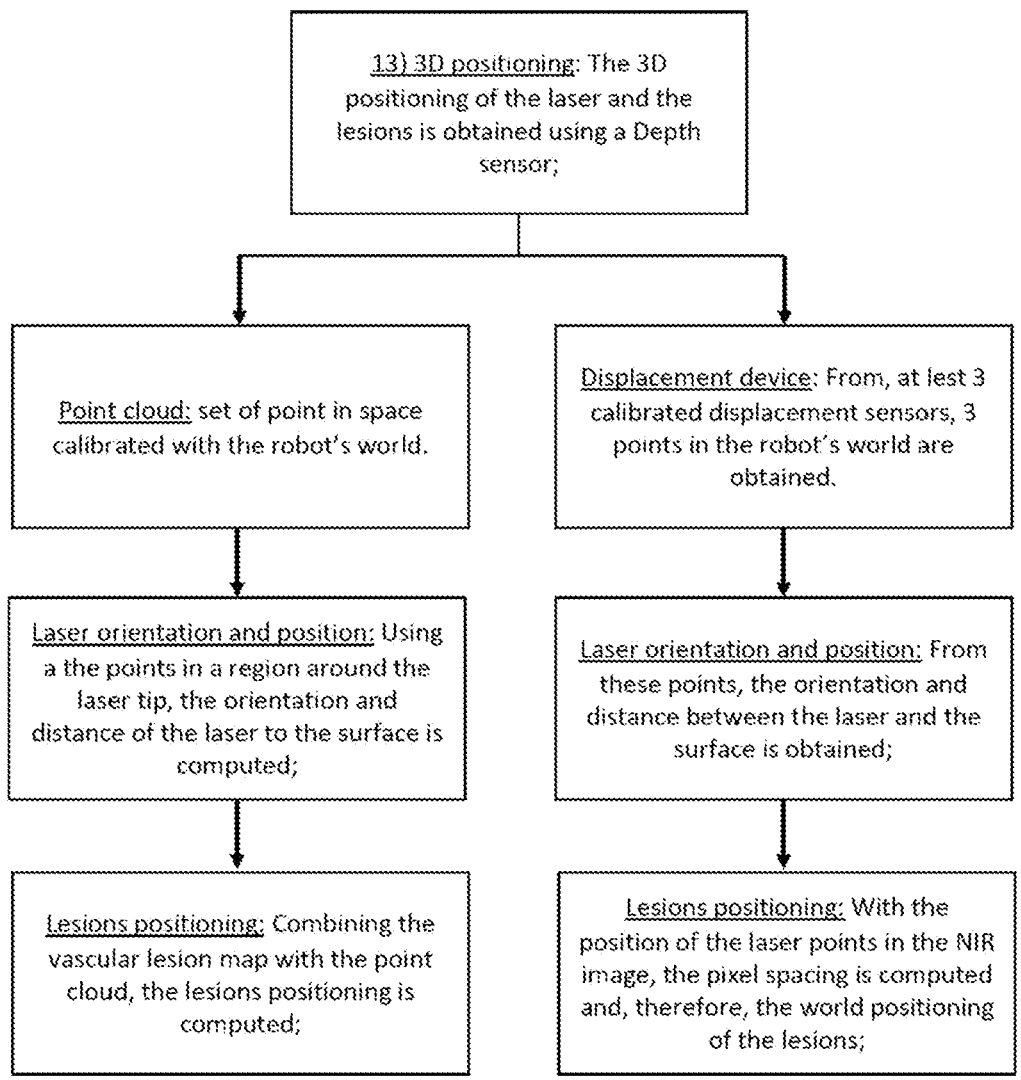
FIG. 11: Schematic representation according to an embodiment of the disclosure of an operation method for 3D positioning with laser-base displacement sensors.
Figure 12:
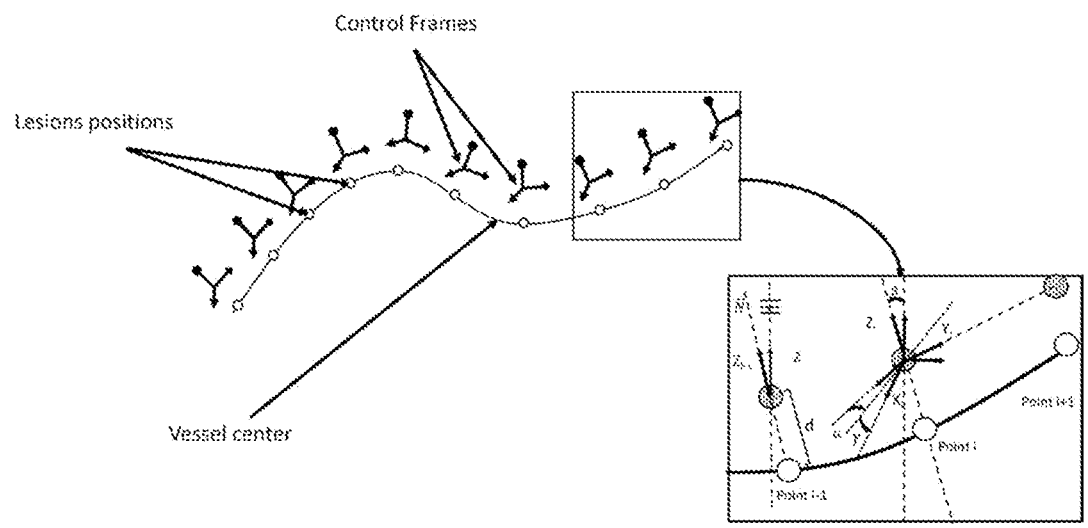
FIG. 12: Schematic illustration according to an embodiment of the disclosure of an operation method for frame-by-frame trajectory planning.
Figure 13:
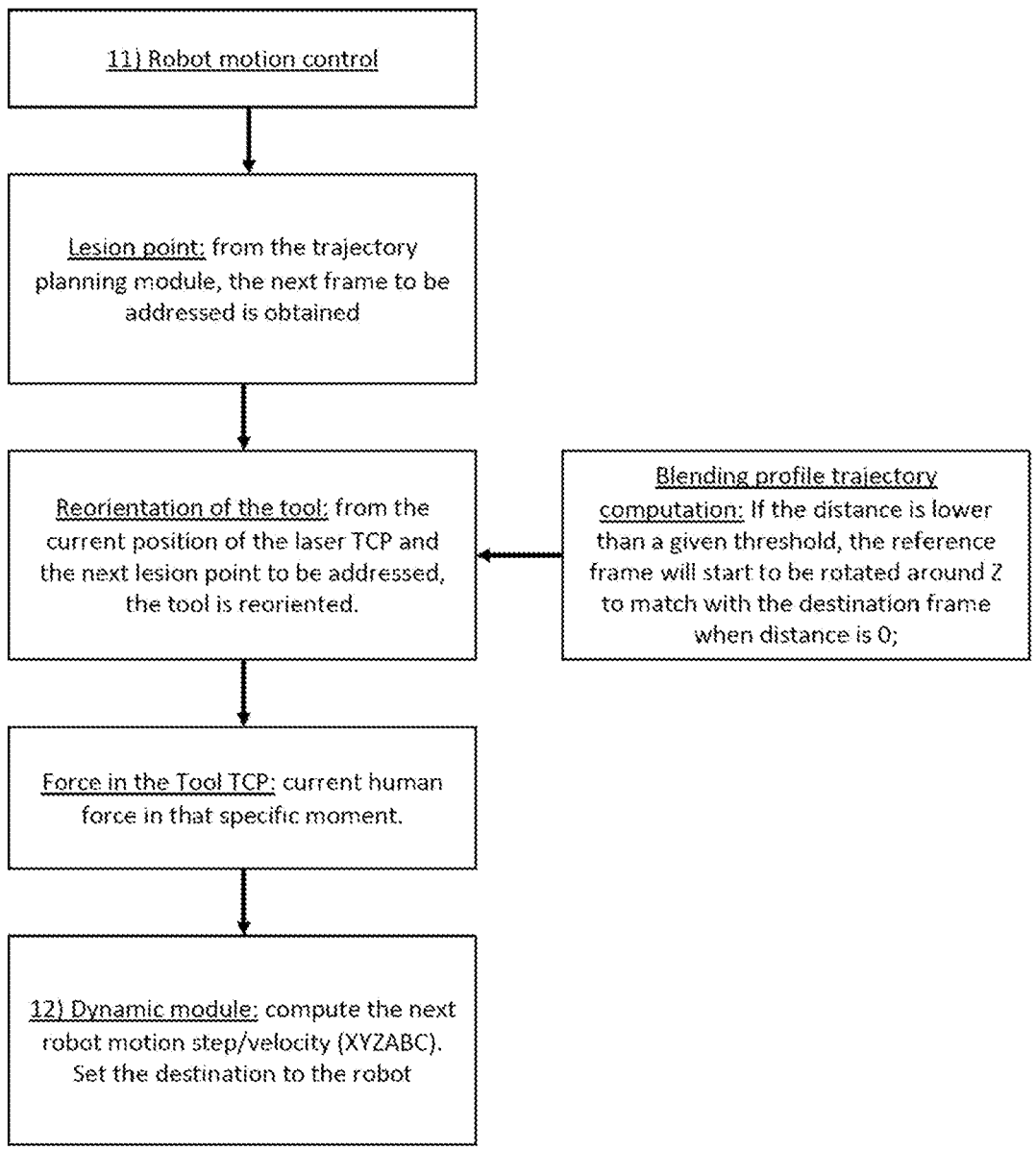
FIG. 13: Schematic representation according to an embodiment of the disclosure of an operation method for robot motion control.
Figure 14:
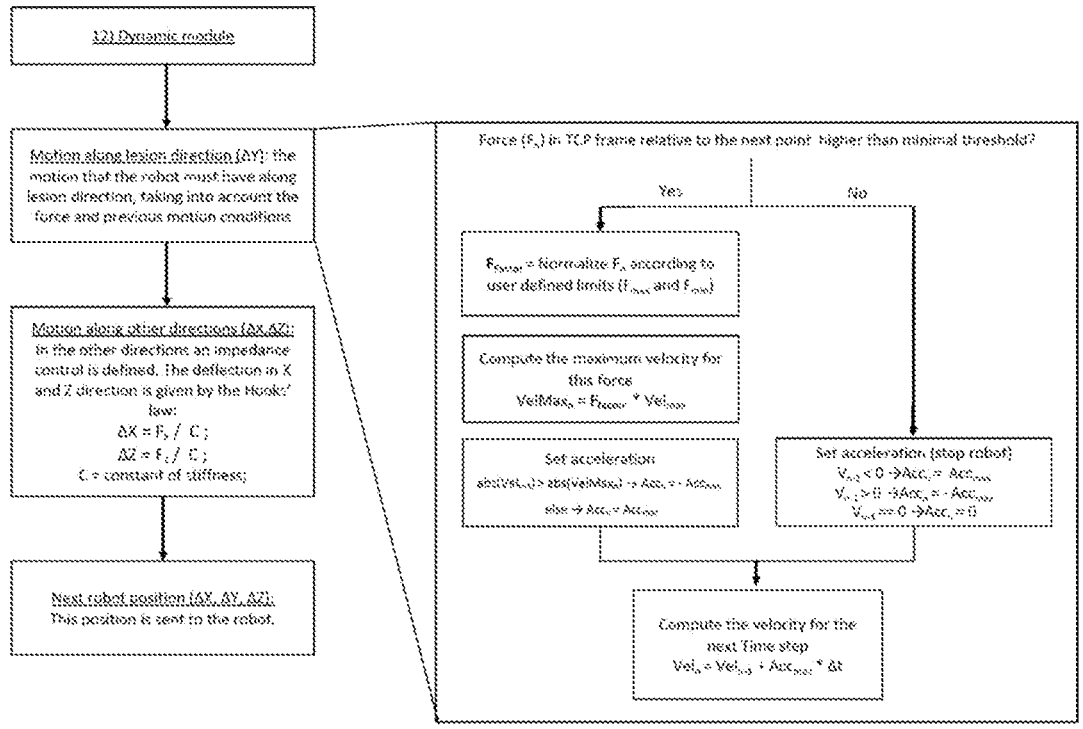
FIG. 14: Schematic representation according to an embodiment of the disclosure of a detailed operation method for robot motion control.
Figure 15:
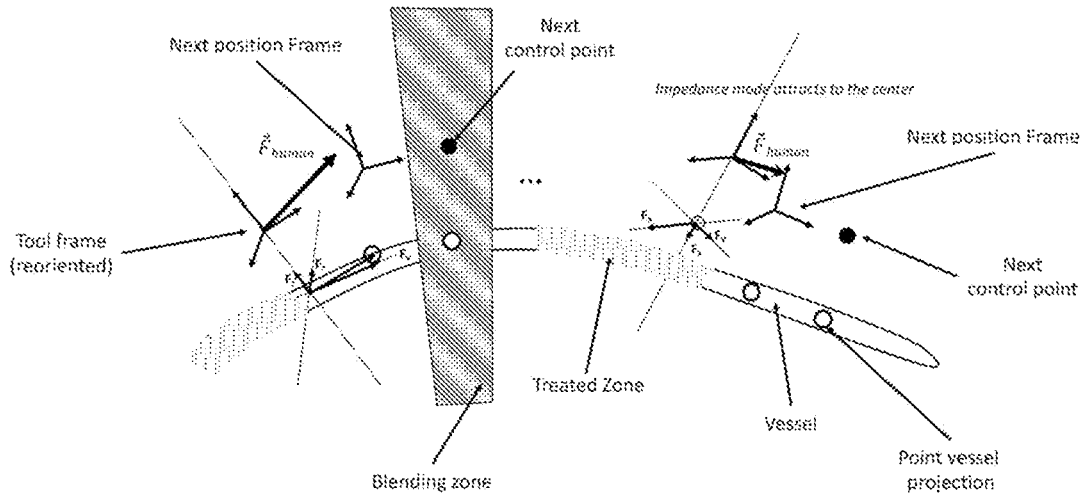
FIG. 15: Schematic illustration according to an embodiment of the disclosure of a frame-by-frame robot motion control.
Figure 16:
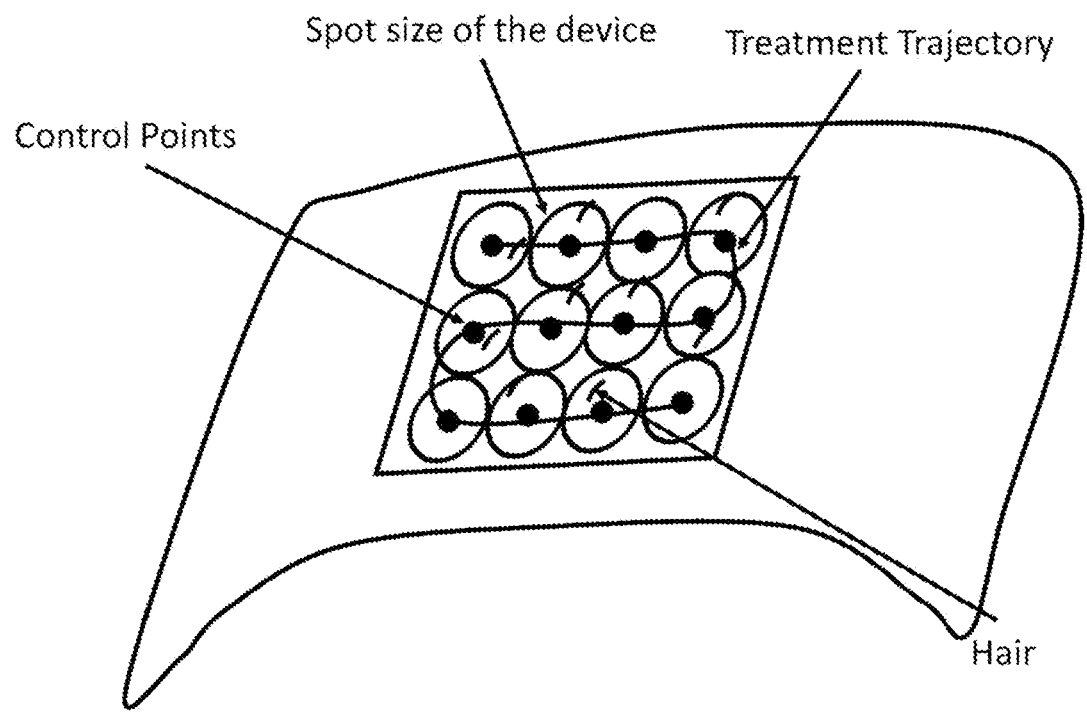
FIG. 16: Schematic illustration according to an embodiment of the disclosure of a skin feature path defined for hair removal.
Figure 17:
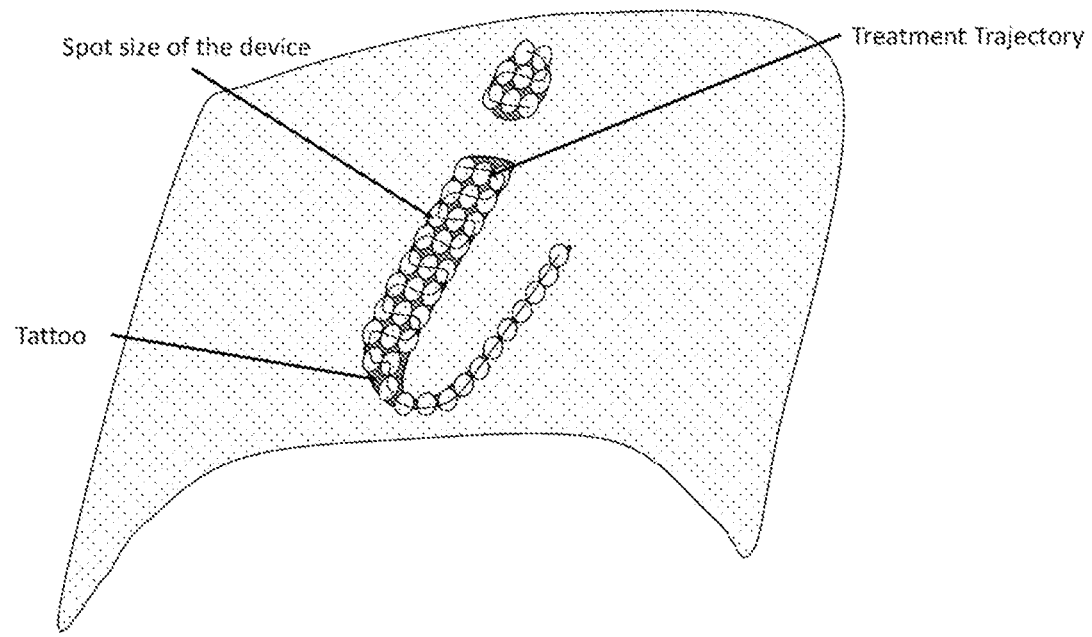
FIG. 17: Schematic illustration according to an embodiment of the disclosure of a skin feature path defined for tattoo removal.

The present disclosure relates to a laser device and a method for operating said device for laser treatment of veins.

According to an embodiment of the disclosure there is a device and method for laser treatment of veins by collaborative motion between an operator and a robotic support, comprising: a vein treatment laser head having a laser beam target line, and a robotic support of said laser head; further comprising, attached to the laser head or to the robotic support where the laser head is supported: a camera for capturing skin surface images, one or more handles for handling by the operator, a force sensor for sensing the intensity and direction of force applied to the handle or handles by the operator for controlling the robotic support, and an electronic data processor configured for carrying out the steps comprising: capturing an image of skin surface comprising a vein to be treated; identifying, from said captured image and proximal to where the laser beam target line intersects the skin surface, the path of the vein to be treated; applying, through the robotic support, a transversal force, to the laser head along a transversal direction to said path and towards said path; while allowing freely controllable movement of the robotic support by the operator along the direction of said path.

The disclosure may be divided into three aspects, namely:
1) laser treatment planning method for location and segmentation of vascular lesions on the patient's leg;
2) real-time laser treatment guidance. A device and method to recognize the laser position on the patient's leg has been developed, later transferring all the planning information into the treatment for a real-time treatment evaluation. The complete treatment setup preferably includes a handheld device that combines both collaborative robot-handling system and a user-friendly monitoring software;
3) setup for the validation of the disclosure. This setup simulates a real person's leg with vascular lesions of interest (i.e. telangiectasias and reticular veins).

The first aspect includes a method and device for planning the treatment of unhealthy leg veins with laser therapy. According to an embodiment of the disclosure there are three camera sensors: (1) RGB images to obtain the leg's texture; (2) NIR for lesion enhancement; and (3) 3D sensor to obtain the distance between laser/patient's skin. Since these camera sensors have independent world spaces, an initial fusion strategy was implemented. Here, at least two images of a known plan pattern (i.e. chessboard) are acquired at the same time from all the cameras.

Then, with this information, it is possible to calibrate each camera (e.g. distortion removal) as well as to infer the transformation matrix that correlates each one of them [2],

[3]. Next, a Deep Learning (DL) strategy has been used to locate and segment all vascular lesions. Here, a convolutional neural network (CNN) architecture that allows a stable performance was designed and further trained.

Although some architectures were already implemented for vessels' segmentation, they just allow one single type of image as input. In this disclosure, we use both RGB/NIR images as input, improving the robustness of the segmentation method. Finally, since the camera's system has limited FoV, it is necessary to capture multiple images to cover all the leg's regions with the desired image quality.

Then, to fuse these set of images into a single one, an image mosaicking strategy is used [4], [5]. In the end, a complete map of all vascular lesions on the patient's leg is obtained. From this map the physician can select the lesions that are to be treated for each specific treatment session, completing the treatment planning strategy. The latter is used to define a laser treatment guidance.

Note that, the implementation of a fully-automatic, robust and accurate strategy for the location and segmentation of vascular lesions within the planned time of work may be not straightforward. Therefore, and as a backup plan, development of semi-automatic tools, where the operator provides small user input to detect the target region, are also valid solution in order to successfully develop the full extent of the described disclosure.

In the second aspect, a treatment guidance system is disclosed. This system incorporates a handheld gripper that combines a monitoring system based on artificial intelligence with the laser device to obtain real-time patient-specific treatment. Moreover, this gripper also allows to plug and play with a collaborative robot.

The first task focuses on a tracking system to obtain real-time positioning of the laser treatment. For it, RGB/NIR images are continuously recorded and analysed using the vascular lesion segmentation module. Since each segmentation pattern of lesions are unique, by fit each with the leg's panoramic view using a registration strategy, the positioning of the camera sensors throughout the treatment is obtained. Consequently, all planning information from the first aspect can be transferred to the treatment, obtaining patient-specific laser treatment guidance.

The next task focuses on the development of a continuous monitoring software of the patient's skin. The treatment guidance visualization and evaluation is achieved using a user-friendly interface. Here, the real-time evaluation is shown in a user-friendly interface, where are planned the following views: (1) patient's skin condition; (2) vascular lesion map over patient's skin; (3) laser position; (4) zoomed view of the vascular lesion map; (5) zoomed view of patient's skin condition. Furthermore, this interface should recognize when the laser focal point is incorrectly positioned and the limits of the lesion to treatment (i.e. vessels clearance).

When any of these situations arise, the physician must be immediately alerted, thus minimizing side effects related to over-treatment [1]. Finally, laser handling assistance is foreseen using a collaborative robot (i.e. LBR Med), helping the physician to guarantee the optimal relation laser/patient's skin over the treatment session. Initially, all the systems (i.e. cameras, laser) are integrated with the robot's end-effector.

Next, different control strategies has been developed to: 1) keep the distance/angle between laser/patient's skin; 2) force the laser positioning at the vessel's centre when near; 3) disable the laser when outside the lesion; and, 4) keep the laser under the limits of pathologic vein that is being treated.

The third aspect module aims to create a setup for the validation of the disclosure. For it, translucid tubes, with diameters ranging from 1-10 mm, is used to simulate the vascular lesions of interest (i.e. telangiectasias and reticular veins). Then, the tubes are placed on the top of a leg of a dummy and after covered with a material to simulate skin properties. Finally, the tubes are filled with a liquid that has the blood characteristics of interest (i.e. colour and absorption of NIR). In the end, a complete setup that simulates a real scenario was achieved, allowing the validation of the developed disclosure.

Specifically for vein treatment, detection techniques have been proposed [6]-[10]. Commonly, these methods combine NIR images with a computer vision (CV) software to obtain real-time guidance [8]-[10]. NIR images were used for vein enhancement, achieving an improvement of >50% in the identification of veins in comparison with a naked-eye evaluation [11], [12]. CV methods automatically locate and segment the veins [7], projecting later this information in the patient's skin and easing its identification [8]-[10]. However, such approaches were mainly focused on venipuncture situations and not on laser-based therapies. Furthermore, a system to help maintain the correct laser handling throughout the treatment is also missing. Although, collaborative robots have previously been described in other applications to facilitate medical treatments, neither was focused on laser treatments for superficial vascular lesions.

The traditional clinical treatment relies on naked eye evaluation while handling the laser device. As such, the treatment outcome is totally dependent of the operator expertise, which is sub-optimal and can results in complications (e.g. discolouration, hypopigmentation, skin texture changes, and scarring), due to incorrect handling of the device or even due to human errors. Moreover, it can also result in an ineffective treatment [1]. As such, a method that guarantees and control the correct handling of a laser equipment during the treatment may minimize the side effects of this treatment, while improving its effectiveness.

Figure 18:
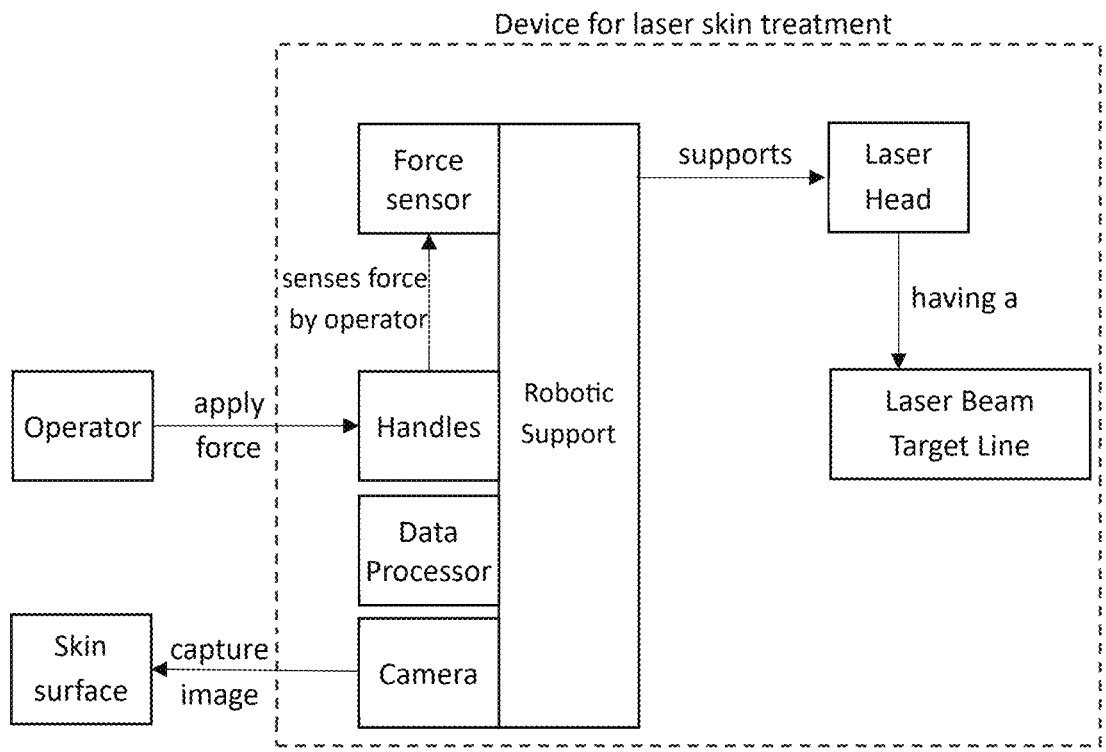
FIG. 18: is a schematic illustration of a device for skin treatment according to an embodiment of the disclosure.
Figure 19:
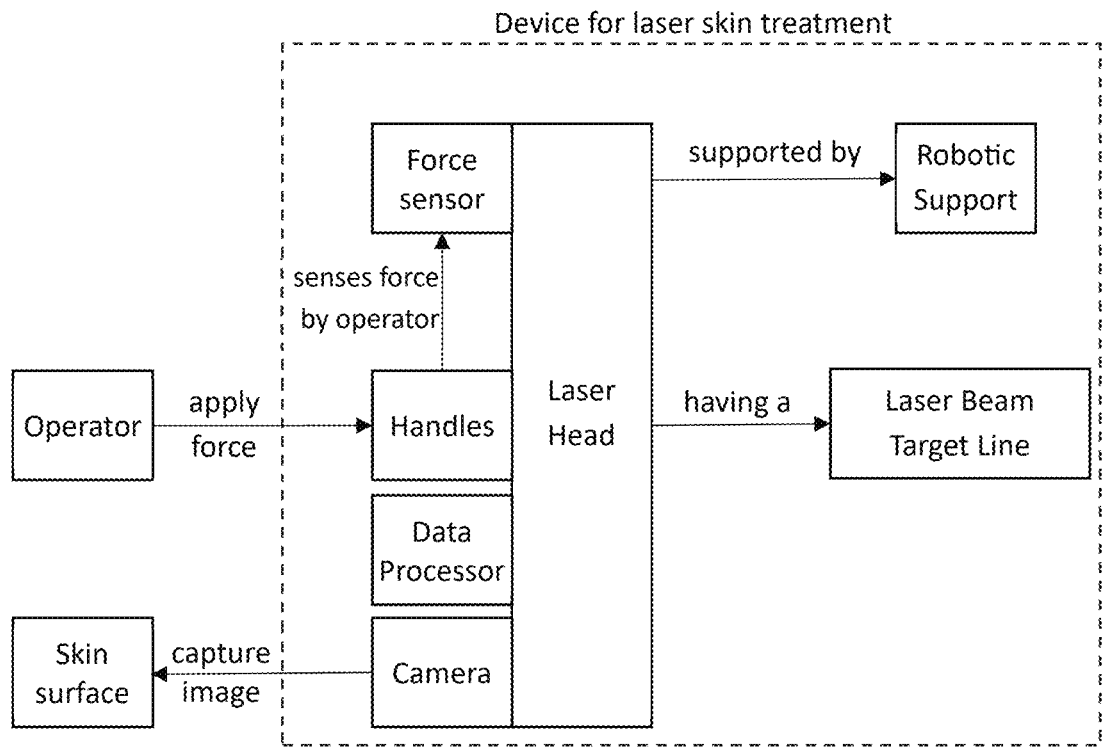
FIG. 19: is a schematic illustration of a device for skin treatment according to another embodiment of the disclosure.

FIGS. 18 and 19 show embodiments of a device for skin treatment. In FIG. 18, a robotic support is coupled to a laser head which emits a laser beam with a target line. An operator can control movement of the robotic support, and thereby the laser head, via handles. A force sensor coupled to the handles provides feedback regarding forces applied by the operator. A camera is coupled to the robotic support which is positioned to capture images of the skin surface of the patient. Images captured by the camera are stored and delivered to an electronic data processor. Additionally, the electronic data processor is coupled to the robotic support so as to control movement of the support, enabling the support and the laser head coupled to the support to follow the path of a skin feature. In the alternative embodiment shown in FIG. 19, the operator directly controls the laser head via handles rather than the robotic support. Similarly, the camera is coupled to the laser head rather than directly to the robotic support. In FIG. 19, the laser head remains coupled to the robotic support for structural stability and movement.

The term "comprising" whenever used in this document is intended to indicate the presence of stated features, integers, steps, components, but not to preclude the presence or addition of one or more other features, integers, steps, components or groups thereof.

It is to be appreciated that certain embodiments of the disclosure as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software, and can be organized as a set of modules, including the various modules and algorithms described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. A device for laser skin treatment of skin features which extend along a path, by which an operator can control a robotic support for the laser skin treatment, the device comprising:
a skin treatment laser head that emits a laser beam along a target line, and a robotic support supporting said laser head;
the device including, attached to the laser head or to the robotic support:
a camera for capturing skin surface images,
one or more handles for handling by the operator,
a force sensor for sensing an intensity and direction of force applied to the handle or handles by the operator for controlling the robotic support, and
an electronic data processor configured for carrying out the steps comprising:
actuating the camera to capture an image of skin surface comprising a skin feature to be treated;
identifying, from said captured image and proximal to where the laser beam target line intersects the skin surface, the path of the skin feature to be treated; and
applying, through the robotic support, a transversal force, to the laser head along a transversal direction to said path and towards said path while allowing freely controllable movement of the robotic support by the operator along the direction of said path.

2. The device for laser skin treatment according to claim 1, wherein said transversal direction is parallel to the skin surface.

3. The device for laser skin treatment according to claim 2, wherein the electronic data processor is further configured for maintaining, through the robotic support, a first transversal distance between said path and where the laser beam target line intersects the skin surface, and wherein said first transversal distance varies positively with a first force as measured by said force sensor along said transversal direction parallel to the skin surface.

4. The device for laser skin treatment according to claim 3, wherein said first transversal distance is directly proportional to said force.

5. The device for laser skin treatment according to claim 1, wherein the electronic data processor is further configured for maintaining, through the robotic support, a second transversal distance between said laser head and skin surface, along a further transversal direction, wherein said further transversal direction is perpendicular to the skin surface, and wherein said second transversal distance, offset by a predetermined amount of distance, varies positively with a second force as measured by said force sensor along said further transversal direction perpendicular to the skin surface.

6. The device for laser skin treatment according to claim 5, wherein said second transversal distance is directly proportional to said further force.

7. The device for laser skin treatment according to claim 6 wherein a proportionality constant of the first transversal distance relative to the first force and a proportionality constant of the second transversal distance relative to the second force are different, and the proportionality constant of the first transversal distance relative to the first force is higher than the proportionality constant of the second transversal distance relative to the second force.

8. The device for laser skin treatment according to claim 1, wherein the electronic data processor is further configured for applying, through the robotic support, a further force to said laser head along a further transversal direction to said path and towards said path, wherein said further transversal direction is perpendicular to the skin surface, such that a second transversal distance between laser head and skin surface is kept constant and equal to a predetermined amount.

9. The device for laser skin treatment according to claim 8, wherein the electronic data processor is further configured for applying, through the robotic support, a further force to said laser head along a further transversal direction to said path and where the laser beam target line intersects the skin surface, such that a second transversal distance between laser head and the laser beam target line is kept constant and equal to a predetermined amount.

10. The device for laser skin treatment according to claim 1 wherein said electronic data processor is further configured for applying a speed dampening to the movement of the robotic support which is inversely related to the speed of the laser head.

11. The device for laser skin treatment according to claim 1, wherein said transversal force is determined by an impedance control in respect of the transversal distance, parallel to the skin surface, between said path and where the laser beam target line intersects the skin surface, versus the force applied by the operator in said transversal direction parallel to the skin surface.

12. The device for laser skin treatment according to claim 1, wherein said transversal force is determined by an impedance control in respect of the transversal distance, perpendicular to the skin surface, between said laser head and skin surface, offset by a predetermined amount of distance, versus the force applied by the operator in said transversal direction perpendicular to the skin surface.

13. The device for laser skin treatment according to claim 1, wherein the electronic data processor is further configured for applying, through the robotic support, a longitudinal force to said laser head along a longitudinal direction along said path, and wherein said force is determined by an impedance control in respect of the longitudinal distance along said path from a predetermined treatment point in respect of the force applied by the operator in said longitudinal direction, wherein the transversal movement stiffness is higher than the longitudinal movement stiffness.

14. The device for laser skin treatment according to claim 1, wherein the force sensor is mounted to sense intensity and direction of the force applied by the operator directly to the handle or handles, or mounted to sense intensity and direction of the force applied by the operator indirectly to the handle or handles by sensing the intensity and direction of force applied by the operator to a joystick mounted on the handle or handles.

15. The device for laser skin treatment according to claim 1 wherein the robotic support is a robotic arm having at least 6 degrees of freedom.

16. The device for laser skin treatment according to claim 1, wherein the electronic data processor is further configured for using low tolerance configurations of the robotic arm degrees of freedom.

17. The device for laser skin treatment according to claim 1, wherein the camera comprises a Near-InfraRed, NIR, camera for vein image capture enhancement.

18. The device for laser skin treatment according to claim 1, wherein the camera comprises a stereoscopic camera, a LIDAR camera or a structured light camera for 3D capture of the skin surface.

19. A method for laser skin treatment of skin features which extend along a path in which an operator can control a robotic support for the laser skin treatment by operating a device comprising a skin feature treatment laser head that emits a laser beam along a target line, and a robotic support of said laser head; further comprising, attached to the laser head or to the robotic support where the laser head is supported, a camera for capturing skin surface images, one or more handles for handling by the operator, a force sensor for sensing the intensity and direction of force applied to the handle or handles by the operator for controlling the robotic support, and an electronic data processor the method comprising:
　using the electronic data processor to carrying out the steps of:
　actuating the camera to capture an image of skin surface comprising a skin feature to be treated;
　identifying, from said captured image and proximal to where the laser beam target line intersects the skin surface, the path of the skin feature to be treated; and
　applying, through the robotic support, a transversal force, to the laser head along a transversal direction to said path and towards said path while allowing freely controllable movement of the robotic support by the operator along the direction of said path.

* * * * *